United States Patent [19]

Bobolev et al.

[11] 3,957,690

[45] May 18, 1976

[54] HETEROGENEOUS CATALYST FOR OXIDATION OF PROPYLENE INTO PROPYLENE OXIDE IN THE LIQUID PHASE AND METHOD FOR PREPARING IT

[76] Inventors: Alexandr Vasilievich Bobolev, Leninsky prospekt, 30, kv. 104; Alexandr Sergeevich Tatikolov, Otkrytoe shosse, 6, korpus 5, kv. 23; Natalya Nikolaevna Lukashina, ulitsa Marii Ulyanovoi, 15, kv. 90; Ivan Stepanovich Krainov, Profsojuznaya ulitsa, 5, kv. 49; Nikolai Markovich Emanuel, Vorobievskoe shosse, 2-b, kv. 42, all of Moscow, U.S.S.R.

[22] Filed: Mar. 14, 1973

[21] Appl. No.: 341,174

[30] Foreign Application Priority Data
Mar. 15, 1972 U.S.S.R............................ 1759606
Mar. 15, 1972 U.S.S.R............................ 1756208

[52] U.S. Cl................................. 252/462; 252/463; 252/464; 252/465; 260/348.5 R
[51] Int. Cl.²..................... B01J 23/10; B01J 23/08; B01J 23/22; B01J 23/28
[58] Field of Search.......... 252/462, 463, 464, 465; 260/348.5 R

[56] References Cited
UNITED STATES PATENTS

| | | | |
|---|---|---|---|
| 1,207,707 | 12/1916 | Bosch et al. | 252/462 |
| 1,935,177 | 11/1933 | Connolly et al. | 252/463 X |
| 1,935,178 | 11/1933 | Connolly | 252/463 X |
| 2,040,782 | 5/1936 | Van Peski | 260/348.5 R |
| 2,129,733 | 9/1938 | Fulton et al. | 252/463 X |
| 2,215,095 | 9/1940 | Drossbach | 252/462 X |
| 2,402,854 | 6/1946 | Thomas | 252/462 X |
| 2,430,443 | 11/1947 | Becker | 260/348.5 R |
| 2,974,161 | 3/1961 | Keith et al. | 252/463 X |
| 3,226,340 | 12/1965 | Stephens et al. | 252/462 X |
| 3,242,069 | 3/1966 | Gladrow et al. | 252/455 R |
| 3,322,491 | 5/1967 | Barrett et al. | 252/462 X |
| 3,353,916 | 11/1967 | Lester | 252/462 X |
| 3,436,409 | 4/1969 | Hill et al. | 260/348.5 R |
| 3,505,359 | 4/1970 | Rai et al. | 260/348.5 R |
| 3,545,917 | 12/1970 | Stephens et al. | 252/462 X |
| 3,760,023 | 9/1973 | Patrick et al. | 252/462 X |

*Primary Examiner*—W. J. Shine
*Attorney, Agent, or Firm*—Haseltine, Lake & Waters

[57] ABSTRACT

A heterogeneous catalyst for oxidation of propylene into propylene oxide in the liquid phase which is a carrier with active components supported thereon, the latter being oxides of scandium, yttrium, indium, gallium, thallium, or rare-earth elements of the lanthanum group, or mixtures of oxides of the above metals. In addition to with said active components, the catalyst can also contain silver, oxides of vanadium, molybdenum, tungsten, bismuth, manganese, or tantalum, or mixtures of the above active components.

The method for preparing the catalyst consists in that the carrier is treated with an aqueous solution of a mineral acid or a mixture of mineral acids at 80° to 100°C, washed with water and dried at 300° to 400°C. The thus treated carrier is impregnated with aqueous solutions of salts of the corresponding metals. The impregnated carrier is treated at a temperature of 700° to 800°C.

The heterogeneous catalyst ensures high selectivity (to 90 per cent) of the process of oxidation of propylene into propylene oxide in the liquid phase, the conversion of propylene being as high as 30 per cent, and also accelerates markedly the process, ensuring a reaction rate 1.5–2 times higher than the reaction rates obtainable with the known catalyst. Furthermore, said catalyst possesses high mechanical strength.

11 Claims, No Drawings

HETEROGENEOUS CATALYST FOR OXIDATION OF PROPYLENE INTO PROPYLENE OXIDE IN THE LIQUID PHASE AND METHOD FOR PREPARING IT

The present invention relates to heterogeneous catalysts for oxidizing propylene into propylene oxide in the liquid phase and also to methods for preparing them.

Known in the prior art are catalysts for liquid-phase oxidation of propylene into propylene oxide, which are actually a carrier with active components applied onto it. For example, known in the art is a heterogeneous catalyst for the liquid-phase oxidation of propylene which is a molybdic zeolite. The method for preparing this catalyst consists in impregnating zeolite with an aqueous solution of ammonium paramolybdate.

Also known in the art is another heterogeneous catalyst for oxidizing propylene into propylene oxide in the liquid phase, which is a carrier with oxides of molybdenum, arsenic and bismuth applied onto it.

The selectivity of the processes for oxidizing propylene into propylene oxide on the known heterogeneous catalysts is low, and the conversion of propylene is insufficiently high. For example, the selectivity of the oxidation process with the former catalyst is 70 per cent, the conversion of the starting propylene being 7.5 per cent. The selectivity of the process with the latter catalyst does not exceed 55 per cent.

It is an object of this invention to provide a heterogeneous catalyst for liquid-phase oxidation of propylene into propylene oxide which would increase the selectivity of the process at a sufficiently high conversion of propylene.

In accordance with this and other objects, the invention consists in that the proposed new catalyst is actually a carrier with the active components, namely, oxides of scandium, yttrium, indium, gallium, thallium, or of rare-earth elements of the lanthanum group, or else mixtures of oxides of the above metals, applied onto its surfaces. The recommended amounts of the active components should be from 5 to 45 per cent calculated as metals with reference to the weight of the carrier.

Moreover, the proposed heterogeneous catalyst can also contain the active component - silver, or oxide of scandium, molybdenum, tungsten, bismuth, manganese, or tantalum, or mixtures of the above active components. The preferable content of silver in the catalyst is from 0.1 to 5 per cent of the carrier weight, and the preferable content of the above oxides in the catalyst, is from 0.1 to 5 per cent calculated as metals with reference to the carrier weight.

The proposed catalyst can be prepared by a method which includes impregnation of the carrier (silica gel, aluminogel, zeolite) with aqueous solutions of salts. According to the invention, in order to increase the activity of the catalyst, said carrier, before being treated with the aqueous solution of salts, is treated with a solution of a mineral acid, for example, hydrochloric or nitric acid, or mixture of mineral acids, at a temperature of 80 to 100°C, washed with water and dried at a temperature of 300° to 400°C. Further treatment of the carrier, according to the invention, consists in impregnating it with aqueous solutions of salts of scandium, yttrium, indium, gallium, thallium or of rare-earth elements of the lanthanum group; or aqueous solutions of mixtures of salts of the abovemetals. The impregnated carrier is then treated at a temperature of 700° to 800°C.

If the carrier is treated with aqueous solutions of salts of various metals, it is recommended to impregnate the carrier successively in each solution and to treat it thermally after impregnating in each solution.

The carrier should be treated with solutions wherein the content of salts should be from 5 to 45 per cent calculated as metals with reference to the carrier weight.

In order to increase the activity of the finished catalyst, it is recommended to impregnate it with an aqueous solution of a salt of silver, vanadium, molybdenum, tungsten, bismuth, manganese, or tantalum, or with aqueous solutions of salts of these metals, after which the catalyst should be treated at a temperature of 700° to 800°C.

If the catalyst is impregnated in aqueous solutions of salts of various metals, it is recommended to treat the catalyst successively in each solution, and to treat it thermally after soaking in each solution.

Solutions for impregnating the catalyst should be taken in amounts which would ensure the content of silver salts therein from 0.1 to 5 per cent calculated as silver with respect to the carrier weight, and the content of salts of vanadium, molybdenum, tungsten, bismuth, manganese, or tantalum, or mixtures of salts of the above metals should be from 0.1 to 5 per cent calculated as metals with reference to the carrier weight.

Unlike the known heterogeneous catalysts, the proposed heterogeneous catalyst ensures high selectivity (90%) of the process of propylene oxidation into propylene oxide in the liquid phase, the conversion of propylene being 30 per cent. The new catalyst accelerates the reaction rate, the latter being about 1.5–2 times as high as that obtained with the known catalysts. Moreover, the proposed catalyst possesses high mechanical strength. Still another advantage of the new catalyst is that the metal oxides can be easily recovered from the surfaces of the carrier by treating the catalyst with dilute nitric acid, and applied onto fresh carrier.

For a better understanding of the invention, examples of preparing the proposed heterogeneous catalyst, and also of its use for liquid-phase oxidation of propylene into propylene oxide, are given hereinafter by way of illustration.

EXAMPLE 1.

100 g of granulated silica gel (particle size - 2 mm) were added to 200 cc of a mixture of hydrochloric and nitric acids taken in the ratio of 1:1 (35 per cent hydrochloric and 50 per cent nitric acids were used for preparing this mixture). The mixture was heated to 100°C and kept at this temperature for 30 minutes with constant stirring. The solution was then decanted, and the carrier washed with water at 80°C to neutral reaction (litmus) and dried at a temperature of 300°C for 30 minutes.

The dried carrier was placed into 100 cc of a 30 per cent (calculated as metal) aqueous solution of scandium nitrate heated to 100°C. The mixture was boiled to evaporate water, after which the carrier with the salt applied onto its surfaces was held at a temperature of 700°C for 40 minutes until nitrogen oxide vapor stopped evolving. The thus prepared catalyst contained 30 per cent of scandium oxide calculated as metal with reference to the carrier weight.

Said catalyst was used for liquid-phase oxidation of propylene into propylene oxide. The oxidation was carried out in a special unit of the autoclave type, in a titanium reactor of 280 ml capacity. The unit was equipped with a water - and carbon dioxide-cooled condenser, a magnetic stirrer of the falling type and a device for taking samples.

Said reactor was loaded with 100 ml of acetone, 25 ml of liquefied propylene and 1 g of the catalyst. The unit was hermetically sealed and air delivered into it from a compressed air cylinder to build up a pressure of 50 atm. The temperature inside the reactor was raised to 170°C, after which air was supplied at a rate of 30 liters per hour. Before being admitted into the reactor, the air was passed through a special device where it was saturated with propylene vapor to ensure constant concentration of propylene in the acetone. In the course of the process, samples were taken from the reactor which were analyzed by chemical methods and by the gas-partition chromatographic method.

Table 1 shows the composition and the yields of the products of propylene oxidation; the reaction was continued for 1 hour.

Table 1

| Reaction product | Concentration of reaction products in reaction mixture, mol/liter | Yeilds of reaction products | |
|---|---|---|---|
| | | mol % of propylene | weight % |
| Propylene oxide | 0.488 | 85.9 | 3.59 |
| Propylene glycol | 0.014 | 2.5 | 0.135 |
| Propylene glycol formate | 0.01 | 2.3 | 0.13 |
| Formic acid | 0.01 | 0.5 | 0.058 |
| Acetic acid | 0.07 | 8.3 | 0.53 |
| Low-boiling products* | — | 0.5 | 0.022 |
| Total | | 100 | |

*In this Table, as well as in the Tables that follow by "low-boiling products" is understood a sum of acetaldehyde, acetone, isopropanol, methanol, methyl formate, and allyl alcohol.

The Table indicates that the yield of propylene oxide was 85.9 mol per cent, the conversion of propylene being 15.8 mol %.

EXAMPLE 2

Silica gel was pretreated with a mixture of hydrochloric and nitric acids under the conditions described in Example 1. Then, the carrier was added to 100 cc of a 30 per cent (calculated as metal) aqueous solution of lanthanum nitrate heated to 100°C. The mixture was boiled to remove water, and the carrier with salt supported thereon was treated at a temperature of 700°C until nitrogen oxide vapor stopped evolving. The finished catalyst contained 30 per cent of lanthanum oxide, calculated as metal with reference to the carrier weight.

Said catalyst was used in the process of propylene oxidation into propylene oxide in the liquid phase. The process was carried out as described in Example 1. Table 2 shows the composition and the yields of the products of propylene oxidation. The reaction was continued for one hour.

Table 2

| Reaction product | Concentration of reaction products in reaction mixture, mol/liter | Yield of reaction products | |
|---|---|---|---|
| | | mol % of propylene | weight % |
| Propylene oxide | 0.49 | 91.2 | 3.6 |
| Propylene glycol | 0.01 | 1.9 | 0.096 |
| Propylene glycol formate | 0.01 | 2.4 | 0.132 |
| Acetic acid | 0.03 | 3.7 | 0.228 |
| Formic acid | 0.01 | 0.6 | 0.058 |
| Low-boiling products | | 0.2 | 0.0073 |
| Total | | 100 | |

The Table shows that the yield of propylene oxide was 91.2 mol per cent and the conversion of propylene was 15.0 mol per cent.

EXAMPLE 3

Silica gel was pretreated with an acid mixture as described in Example 1. The carrier was then added to 100 cc of a 30 per cent (as metal) aqueous solution of europium nitrate heated to 100°C. The mixture was then boiled to remove water, after which the carrier with salt supported thereon was treated at a temperature of 800°C for 40 minutes In order to apply another active component, the catalyst was immersed into 100 cc of a 10 per cent (calculated as metal) aqueous solution of thallium nitrate. The mixture was evaporated and treated at a temperature of 800°C until the vapor of hydrogen stopped evolving. The thus prepared catalyst contained 30 per cent of europium oxide and 10 per cent of thallium oxide calculated as metals with reference to the carrier weight.

Said catalyst was used in the process of oxidation of propylene into propylene oxide in the liquid phase. The process was carried out as described in Example 1. The reaction was continued for 1 hour.

Table 3

| Reaction products | Concentration of reaction products in reaction mixture, mol/liter | Yields of reaction products | |
|---|---|---|---|
| 1 | 2 | mol % of propylene | weight % |
| | | 3 | 4 |
| Propylene oxide | 0.52 | 90.3 | 3.82 |
| Propylene glycol | 0.012 | 2.1 | 0.115 |
| Propylene glycol formate | 0.009 | 2.1 | 0.119 |
| Acetic acid | 0.04 | 4.7 | 0.304 |
| Formic acid | 0.01 | 0.5 | 0.058 |
| Low-boiling products | | 0.3 | 0.015 |
| Total | | 100 | — |

The Table shows that the yield of propylene oxide was 90.3 mol per cent and the conversion of propylene was 16.0 mol per cent.

EXAMPLE 4

Zeolite CaY was pretreated with acid as described in Example 1. The carrier was then immersed into 100 cc of a 30 per cent (calculated as metal) aqueous solution of neodymium nitrate heated to 80°C. The mixture was then evaporated at said temperature to remove water. The impregnated carrier was treated at a temperature of 700°C for 40 minutes until the vapor of nitrogen oxide stopped evolving. In order to apply the other active component, the catalyst was immersed into 100 cc of a 2.5 per cent (as metal) aqueous solution of silver nitrate. The mixture was evaporated to remove water, after which it was treated at a temperature of 700°C until the nitrogen oxides stopped evolving. The finished catalyst contained 30 per cent of neodymium oxide calculated as metal with reference to the carrier weight, and 2.5 per cent of silver with respect to the carrier weight.

Said catalyst was used in the process for oxidation of propylene into propylene oxide in the liquid phase. The process was carried out under the conditions described in Example 1, except that the temperature during the reaction was maintained at 145°C, and the solvent was methyl ethyl ketone.

Table 4 shows the composition and the yields of the products of propylene oxidation; the reaction was continued for 1 hour.

Table 4

| Reaction product | Concentration of reaction products in reaction mixture, mol/liter | Yield of reaction products mol % of propylene | weight % |
| --- | --- | --- | --- |
| Propylene oxide | 0.465 | 81.8 | 3.42 |
| Propylene glycol | 0.015 | 2.6 | 0.14 |
| Propylene glycol formate | 0.01 | 2.3 | 0.13 |
| Acetic acid | 0.10 | 12.3 | 0.76 |
| Formic acid | 0.01 | 0.5 | 0.058 |
| Low-boiling products | — | 0.5 | 0.022 |
| Total | | 100 | — |

The Table shows that the yield of propylene oxide was 81.8 mol per cent, the conversion of propylene being 15.8 mol per cent.

EXAMPLE 5

Silica gel was pretreated with acids as described in Example 1. Then the carrier was immersed into 100 cc of a 30 per cent (as metal) aqueous solution of gadolinium nitrate heated to 100°C. The mixture was boiled to remove water, and the carrier with salt supported thereon was treated at a temperature of 800°C for 40 minutes. In order to apply the second active component, the catalyst was immersed into 100 cc of a 2 per cent (calculated as metal) aqueous solution of bismuth nitrate. The mixture was evaporated to remove water, after which it was treated at a temperature of 800°C until the nitrogen oxides stopped evolving. The thus prepared catalyst contained 30 per cent of gadolinium oxide and 2 per cent of bismuth oxide calculated as metals with respect to the carrier weight.

Said catalyst was used in the process for oxidation of propylene into propylene oxide in the liquid phase. The process was carried out under the conditions described in Example 1.

Table 5 shows the composition and the yields of the products of propylene oxidation. The reaction was continued for 1 hour.

Table 5

| Reaction product | Concentration of reaction products in reaction mixture, mol/liter | Yields of reaction products mol % of propylene | weight % |
| --- | --- | --- | --- |
| Propylene oxide | 0.46 | 91.2 | 3.38 |
| Propylene glycol | 0.013 | 2.6 | 0.125 |
| Propylene glycol formate | 0.01 | 2.6 | 0.132 |
| Acetic acid | 0.02 | 2.6 | 0.152 |

Table 5-continued

| Reaction product | Concentration of reaction products in reaction mixture, mol/liter | Yields of reaction products mol % of propylene | weight % |
| --- | --- | --- | --- |
| Formic acid | 0.01 | 0.6 | 0.058 |
| Low-boiling products | — | 0.4 | 0.015 |
| Total | | 100 | — |

The Table shows that the yield of propylene oxide was 91.2 mol per cent, the conversion of propylene being 14 mol per cent.

EXAMPLE 6

Silica gel was given acid treatment under the conditions described in Example 1. The carrier was then immersed into 100 cc of a 25 per cent (calculated as metal) aqueous solution of neodymium nitrate heated to 100°C. The mixture was then evaporated to remove water, after which the carrier with salt supported thereon was treated at a temperature of 700°C until nitrogen oxides stopped evolving. In order to apply the second active component, the catalyst was immersed into 100 cc of a 5 per cent (calculated as metal) aqueous solution of tantalum acetate. The mixture was evaporated to remove water, after which it was treated at a temperature of 700°C until nitrogen oxides stopped evolving. For the application of the third active component, the catalyst was immersed into 100 cc of a 2.5 per cent (calculated as metal) aqueous solution of silver nitrate. The mixture was evaporated to remove water, after which it was treated at a temperature of 700°C until nitrogen oxides stopped evolving. The finished catalyst contained 25 per cent of neodymium oxide and 5 per cent of tantalum oxide calculated as metals with respect to the carrier weight, and also 2.5 per cent of silver calculated with reference to the carrier weight. The catalyst was used in the process of oxidation of propylene into propylene oxide in the liquid phase. The process was carried out under the conditions described in Example 1.

Table 6 shows the composition and the yields of the products of propylene oxidation; the reaction was continued for 1 hour.

Table 6

| Reaction products | Concentration of reaction products in reaction mixture, mol/liter | Yields of reaction products mol % of propylene | weight % |
| --- | --- | --- | --- |
| Propylene oxide | 0.50 | 86.5 | 3.68 |
| Propylene glycol | 0.02 | 3.5 | 0.19 |
| Propylene glycol formate | 0.015 | 3.5 | 0.20 |
| Acetic acid | 0.10 | 5.7 | 0.76 |
| Formic acid | 0.01 | 0.5 | 0.058 |
| Low-boiling products | — | 0.3 | 0.015 |
| Total | | 100 | — |

The Table shows that the yield of propylene oxide was 86.5 mol per cent, the conversion of propylene being 17.4 mol %.

EXAMPLE 7

Silica gel was given acid treatment under the conditions described in Example 1, except that a 50 per cent nitric acid was used. The carrier was then immersed into 100 cc of a 5 per cent (calculated as metal) aqueous solution of europium nitrate heated to 100°C. The mixture as then evaporated to remove water, after which the carrier with salt supported thereon was treated at a temperature of 700°C for 40 minutes until nitrogen oxide vapor stopped evolving. The finished catalyst contained 5 per cent of europium oxide calculated as metal with reference to the carrier weight.

The catalyst was used in the process of propylene oxidation into propylene oxide in the liquid phase. The process was carried out under the conditions described in Example 1. Table 7 shows the composition and the yields of the products of propylene oxidation; the reaction was continued for 1 hour.

Table 7

| Reaction product | Concentration of reaction products in reaction mixture, mol/liter | Yield of reaction products | |
| --- | --- | --- | --- |
| | | mol % of propylene | weight % |
| Propylene oxide | 0.42 | 90.0 | 3.0 |
| Propylene glycol | 0.01 | 2.1 | 0.096 |
| Propylene glycol formate | 0.01 | 2.8 | 0.132 |
| Acetic acid | 0.03 | 4.3 | 0.228 |
| Formic Acid | 0.01 | 0.6 | 0.058 |
| Low-boiling products | — | 0.2 | 0.0073 |
| Total | | 100 | |

The Table shows that the yield of propylene oxide was 90.0 mol per cent, the conversion of propylene being 13 mol per cent.

EXAMPLE 8

Aluminogel was given acid treatment under the conditions described in Example 1. The carrier was then immersed into 100 cc of a 10 per cent (calculated as metal) aqueous solution of gadolinium nitrate heated to 100°C. The mixture was boiled to remove water, after which the carrier with salt supported thereon was treated at a temperature of 700°C for 40 minutes. In order to apply the second active component, the catalyst was immersed into 100 cc of a 10 per cent (calculated as metal) aqueous solution of europium nitrate. The mixture was evaporated to remove water, after which it was held at a temperature of 700°C until nitrogen oxide vapor stopped evolving. The prepared catalyst contained 10 per cent of gadolinium oxide and 10 per cent of europium oxide calculated as metals with reference to the carrier weight.

Said catalyst was used in the process of propylene oxidation into propylene oxide in the liquid phase. The process was carried out under conditions similar to those of Example 1.

Table 8 shows the composition and the yields of the products of propylene oxidation; the reaction was continued for 1 hour.

Table 8

| Reaction product | Concentration of reaction products in reaction mixture, mol/liter | Yield of reaction products | |
| --- | --- | --- | --- |
| | | mol % of propylene | weight % |
| Propylene oxide | 0.78 | 88.0 | 5.7 |
| Propylene glycol | 0.015 | 1.6 | 0.14 |
| Propylene glycol formate | 0.01 | 1.5 | 0.13 |
| Acetic acid | 0.11 | 7.9 | 0.84 |
| Formic acid | 0.01 | 0.4 | 0.058 |
| Low-boiling products | — | 0.6 | 0.037 |
| Total | — | 100 | — |

The Table shows that the yield of propylene oxide was 88.0 mol per cent, the degree of propylene conversion being 24.6 mol per cent.

EXAMPLE 9

Silica gel was given acid treatment under the conditions described in Example 1. The carrier was then immersed into 100 cc of a 30 per cent (calculated as metal) aqueous solution of gadolinium nitrate heated to 100°C. The mixture was evaporated to remove water, after which the carrier with salt supported thereon was held at a temperature of 800°C until the nitrogen oxide vapor stopped evolving. In order to apply the second active component, the catalyst was immersed into 100 cc of a 4 per cent (calculated as metal) aqueous solution of a molybdenum salt prepared by dissolving 6.7 g of molybdic acid in a mixture of hydrochloric and nitric acids. The mixture was then evaporated to remove the acids and water, after which it was held at a temperature of 800°C until the nitrogen oxide vapors stopped evolving. The finished catalyst contained 30 per cent of gadolinium oxide and 4 per cent of molybdenum oxide, calculated as metals with respect to the carrier weight.

Said catalyst was used in the process of oxidation of propylene into propylene oxide in the liquid phase. The process was carried out under the conditions described in Example 1.

Table 9 shows the composition and the yields of the products of propylene oxidation. The reaction was continued for 1 hour.

Table 9

| Reaction product | Concentration of reaction products in reaction mixture, mol/liter | Yield of reaction products | |
| --- | --- | --- | --- |
| | | mol % of propylene | weight % |
| Propylene oxide | 0.452 | 92.2 | 3.33 |
| Propylene glycol | 0.015 | 3.1 | 0.14 |
| Propylene glycol formate | 0.012 | 3.3 | 0.16 |
| Acetic acid | 0.009 | 1.2 | 0.63 |
| Formic acid | 0.001 | 0.1 | 0.006 |
| Low-boiling products | — | 0.1 | 0.004 |
| Total | | 100.0 | |

The Table shows that the yield of propylene oxide was 92.2 mol per cent, and the conversion of propylene was 13.6 mol per cent.

EXAMPLE 10

Silica gel was given acid treatment under the conditions described in Example 1. The carrier was then immersed into 100 cc of a 30 per cent (calculated as metal) aqueous solution of europium nitrate heated to 80°C. The mixture was boiled to remove water, after which the carrier with salt supported thereon was treated at a temperature of 700°C for 40 minutes. The second active component was applied onto the catalyst by immersing it into 100 cc of a 2.5 per cent (calculated as metal) aqueous solution of silver nitrate. The mixture was evaporated to remove water, after which it was treated at a temperature of 800°C until nitrogen oxide vapors stopped evolving. The finished catalyst contained 30 per cent of europium oxide calculated as metal with respect to the carrier weight and 2.5 per cent of silver with respect to the carrier weight.

Said catalyst was used in the process of oxidation of propylene into propylene oxide in the liquid phase. The process was carried out under the conditions described in Example 1.

Table 10 shows the composition and the yields of the products of propylene oxidation; the reaction was continued for 2 hours.

Table 10

| Reaction product | Concentration of reaction products in reaction mixture, mol/liter | Yield of reaction products | |
|---|---|---|---|
| | | mol % of propylene | weight % |
| Propylene oxide | 1.06 | 90.7 | 7.80 |
| Propylene glycol | 0.018 | 1.5 | 0.17 |
| Propylene glycol formate | 0.015 | 1.7 | 0.20 |
| Acetic acid | 0.10 | 5.1 | 0.76 |
| Formic acid | 0.02 | 0.6 | 0.12 |
| Low-boiling products | — | 0.4 | 0.04 |
| Total | | 100 | |

The Table shows that the yield of propylene oxide was 90.7 mol per cent, and the conversion of propylene was 32.5 mol per cent.

What is claimed is:

1. A heterogeneous catalyst for oxidation of propylene into propylene oxide in the liquid phase, which is a mineral acid-modified carrier with at least one active component supported thereon, said active component being an oxide of a metal selected from the group consisting of scandium, yttrium, indium, gallium, thallium, and rare-earth elements of the lanthanum group, wherein said carrier was modified by treating with an aqueous solution of a mineral acid or mixture of mineral acids at 80° to 100°C., washing with water and drying at 300° to 400°C.

2. A heterogeneous catalyst as claimed in claim 1, containing said active component in an amount from 5 to 45 per cent calculated as metal with respect to the carrier weight.

3. A heterogeneous catalyst as claimed in claim 1, which also contains at least one additional active component selected from the group consisting of silver, vanadium oxide, molybdenum oxide, tungsten oxide, bismuth oxide, manganese oxide, and tantalum oxide.

4. A heterogeneous catalyst as claimed in claim 3, containing said additional active component in an amount from 0.1 to 5 per cent calculated as metal with respect to the carrier weight.

5. A method for preparing a heterogeneous catalyst for oxidation of propylene into propylene oxide in the liquid phase consisting in that the carrier is treated with an aqueous solution of mineral acid at a temperature of 80° to 100°C, washed with water and dried at a temperature of 300° to 400°C; the thus treated carrier is impregnated with an aqueous solution of a salt of at least one metal selected from the group consisting of scandium, yttrium, indium, gallium, thallium, and rare-earth elements of the lanthanum group; and the impregnated carrier is treated at a temperature of 700° to 800°C.

6. A method as claimed in claim 5, wherein the treated carrier is impregnated successively with aqueous solutions of salts of various said metals with subsequent thermal treatment thereof.

7. A method as claimed in claim 5, wherein the carrier is impregnated with an aqueous solution of a salt taken in an amount of salt content from 5 to 45 per cent calculated as metal with respect to the carrier weight.

8. A method as claimed in claim 5, wherein the finished catalyst is impregnated with an aqueous solution of a salt of a metal selected from the group consisting of silver, vanadium, molybdenum, tungsten, bismuth, manganese, and tantalum, after which the catalyst is treated at a temperature of 700° to 800°C.

9. A method as claimed in claim 8, wherein the catalyst is impregnated successively with aqueous solutions of salts of various said metals with subsequent thermal treatment thereof.

10. A method as claimed in claim 8, wherein the salt content is from 0.1 to 5 per cent calculated as metal with respect to the carrier weight.

11. A heterogeneous catalyst for oxidation of propylene into propylene oxide in the liquid phase, which is a mineral acid-modified carrier with at least one active component supported thereon, said active component being an oxide of a metal selected from the group consisting of scandium, yttrium, indium, and gallium.

* * * * *